United States Patent
Lee et al.

(10) Patent No.: US 11,458,204 B2
(45) Date of Patent: Oct. 4, 2022

(54) METHOD FOR IMPROVING SUBSTITUTION RATE AND/OR SUBSTITUTION EFFICIENCY OF HYALURONAN-DRUG CONJUGATES

(71) Applicant: Aihol Corporation, Artesia, CA (US)

(72) Inventors: Szu-Yuan Lee, Taipei (TW); Ping-Shan Lai, Taipei (TW); Chih-An Lin, Taipei (TW)

(73) Assignee: Aihol Corporation, Buena Park, CA (US)

( * ) Notice: Subject to any disclaimer, the term of this patent is extended or adjusted under 35 U.S.C. 154(b) by 8 days.

(21) Appl. No.: 17/117,231

(22) Filed: Dec. 10, 2020

(65) Prior Publication Data

US 2021/0369852 A1    Dec. 2, 2021

Related U.S. Application Data

(63) Continuation-in-part of application No. 16/891,020, filed on Jun. 2, 2020.

(51) Int. Cl.
A61K 47/61 (2017.01)

(52) U.S. Cl.
CPC ..................................... A61K 47/61 (2017.08)

(58) Field of Classification Search
CPC ............................ A61K 47/61; C08B 37/0072
See application file for complete search history.

(56) References Cited

U.S. PATENT DOCUMENTS

| | | |
|---|---|---|
| 2009/0054537 A1 | 2/2009 | Brown |
| 2010/0144035 A1 | 6/2010 | Oh et al. |
| 2012/0294945 A1 | 11/2012 | Hahn et al. |
| 2013/0116411 A1 | 5/2013 | Pollock et al. |
| 2015/0065446 A1 | 3/2015 | Lin |
| 2019/0015518 A1 | 1/2019 | Forrest et al. |
| 2019/0328891 A1 | 10/2019 | Karel et al. |

FOREIGN PATENT DOCUMENTS

| | | |
|---|---|---|
| KR | 20170010651 A | 2/2017 |
| WO | 2011/148116 A2 | 12/2011 |

OTHER PUBLICATIONS

Norbedo (Carbohydrate Research; 2009, 344, 98-104).*
Sigma-Aldrich (DMSO product specification, https://www.sigmaaldrich.com/specification-sheets/634/230/276855-BULK_____SIAL____.pdf, downloaded on May 24, 2022).*

* cited by examiner

*Primary Examiner* — Pancham Bakshi
(74) *Attorney, Agent, or Firm* — Patenttm.us

(57) ABSTRACT

Disclosed herein is a method for preparing a hyaluronan-drug conjugate. The method uses the ethyl cyano(hydroxyimino)acetate/diisopropylcarbodiimide coupling system in a homogeneous reaction phase, which unexpectedly improves the substitution rate and substitution efficiency of hyaluronan-drug conjugates for various drugs.

19 Claims, No Drawings

METHOD FOR IMPROVING SUBSTITUTION RATE AND/OR SUBSTITUTION EFFICIENCY OF HYALURONAN-DRUG CONJUGATES

CROSS REFERENCE TO RELATED APPLICATIONS

This application is a continuation in part application of U.S. patent application filed on Jun. 2, 2020 and having application Ser. No. 16/891,020, the entire contents of which are hereby incorporated herein by reference.

BACKGROUND OF THE INVENTION

1. Field of the Invention

The present disclosure, in general, relates to methods for synthesizing hyaluronic acid (HA)-drug conjugates, particularly to methods for improving the substitution rate and/or substitution efficiency of HA-drug conjugates.

2. Description of Related Art

Hyaluronic acid (HA) (also called hyaluronate or hyaluronan) has been investigated as a novel drug carrier for various small molecule drugs or therapeutic proteins/peptides. HA is an anionic, nonsulfated glycosaminoglycan composed of a repeating sequence of disaccharide units, specifically a D-glucuronic acid and an N-acetyl-D-glucosamine (–4GlcUAβ1-3GlcNAcβ1-). Its molecular weight can range from 379 Dalton (Da) (the single disaccharide unit) to several millions of Daltons.

In some applications, hyaluronan has been conjugated with therapeutic molecules (such as cytotoxic drugs and anti-inflammatory drugs). However, the efficiency of HA-drug conjugation is often dissatisfactory due to the spatial hindrance and the reactivity of the available functional groups. Although various linkers are proposed to address the issue as mentioned earlier, the effectiveness is still limited.

Given the foregoing, there exists in the related art a need for a synthesis method with improved substitution rate and/or substitution efficiency of HA-drug conjugates.

SUMMARY

The following presents a simplified summary of the disclosure to provide a basic understanding to the reader. This summary is not an extensive overview of the disclosure, and it does not identify key/critical elements of the present invention or delineate the scope of the present invention. Its sole purpose is to present some concepts disclosed herein in a simplified form as a prelude to the more detailed description presented later.

In one aspect, the present disclosure is directed to a method for synthesizing HA-drug conjugates. Specifically, methods according to embodiments of the present disclosure employ the ethyl cyano(hydroxyimino)acetate (Oxyma)/diisopropylcarbodiimide (DIC) coupling system in a homogeneous reaction phase comprising water and dimethyl sulfoxide (DMSO). According to the principles and spirits of the present disclosure, DMSO, serving as a co-solvent, allows the components in the reaction system to react in a homogeneous reaction phase while at the same time avoids the re-arrangement issue experienced in the water phase reaction system using EDC/NHS. In this way, the present methods significantly improve the substitution rate and/or substitution efficiency for synthesizing various HA-drug conjugates.

According to various embodiments of the present disclosure, the method for synthesizing a hyaluronan-drug conjugate includes the following steps: preparing a drug solution by dissolving a plurality of drug molecules in DMSO; preparing an additive solution by dissolving an additive in DMSO; preparing a hyaluronan solution by dissolving a plurality of hyaluronan molecules in distilled water and DMSO; mixing the drug solution, the additive solution, the hyaluronan solution and DIC to obtain a reaction mixture; and allowing components in the reaction mixture to react, thereby forming the hyaluronan-drug conjugate.

In some optional embodiments, the additive is capable of facilitating the formation of an activated ester. In particular, the additive can facilitate the formation of an activated ester while reducing the racemization. Examples of such additives include ethyl cyano(hydroxyimino)acetate, hydroxybenzotriazole (HOBt), and N-hydroxysuccinimide (NHS).

According to some optional embodiments of the present disclosure, at least one of the drug molecules has or is modified to have at least one amino group. In some embodiments, the amino group is a primary amine. In some embodiments, the drug molecule is modified with one or more amino acids (e.g., S-alanine (β-Ala) or glycine) or urea.

In certain optional embodiments, when at least one of the drug molecules is modified to have a primary amine, the step of mixing the drug solution, the additive solution, the hyaluronan solution and DIC comprises the steps of, preparing a hyaluronan/additive solution by mixing the additive solution with the hyaluronan solution; mixing the drug solution with the hyaluronan/additive solution; and adding DIC into the hyaluronan/additive solution.

According to some other optional embodiments of the present disclosure, at least one of the drug molecules has or is modified to have a carboxylate group. In some embodiments, the drug molecule is modified with a $C_2$-$C_{20}$ dicarboxylic acid. In some other embodiments, the hyaluronan molecule is modified with a linker, such as a dihydrazide (e.g., adipic acid dihydrazide (ADH)).

According to some embodiments of the present disclosure, the hyaluronan molecules have a weight-average molecular weight (Mw) of about 5 kilodaltons (kDa) to 500 kDa. According to various embodiments, the hyaluronan molecule is a hyaluronic acid (HA) molecule, or a derivative or salt thereof.

According to some optional embodiments of the present disclosure, the hyaluronan-drug conjugate has a degree of substitution with the drug molecule of 0.5 to 70%. According to some other optional embodiments of the present disclosure, the hyaluronan-drug conjugate has a substitution efficiency of at least 20%.

According to various embodiments of the present disclosure, the drug molecule is a steroid drug, nucleoside or nucleotide analog, non-steroid anti-inflammatory drug (NSAID), a cytotoxic drug, or immunomodulator. For example, the steroid drug is cholesterol, cortisone, hydrocortisone, prednisolone, methylprednisolone, dehydroepiandrosterone, triamcinolone, dexamethasone, betamethasone, triamcinolone acetonide, budesonide, estrone, estradiol, estriol, testosterone or 11-deoxycorticosterone. Non-limiting examples of the nucleoside or nucleotide analog include deoxyadenosine analogs, adenosine analogs, deoxycytidine analogs, guanosine analogs, deoxyguanosine analogs, thymidine analogs, deoxythymidine analogs, and deoxyuridine analogs. Illustrative examples of NSAID include, but are not limited to, aspirin, ibuprofen, nimesulide, diclofenac, mefenamic acid, naproxen, sulindac, ketorolac, ketoprofen, tenoxicam, indomethacin, valdecoxib, celecoxib, etoricoxib, and rofecoxib. Cytotoxic drugs can be, such an azacytidine, belinostat, bendamustine, brentuximab vedotin, bleomycin, bortezomib, busulfan, carboplatin, carmustine, cyclophosphamide, cytarabine, dacarbazine, dactinomycin, daunorubicin, decitabine, deferoxamine, doxorubicin, epirubicin hydrochloride, fludarabine, fotemustine, fulvestrant, gemcitabine, idarubicin, ifosfamide, irinotecan hydrochloride, ixabepilone, melphalan, methotrexate, oxaliplatin, paclitaxel, pemetrexed, pentostatin, raltitrexed, romidepsin, temozolomide, thiotepa, topotecan, trabectedin, trastuzumab, or vinblastine. Examples of immunomodulators include, but are not limited to, lenalidomide, pomalidomide, and thalidomide.

Many of the present disclosure's attendant features and advantages will become better understood with reference to the following detailed description considered in connection with the accompanying drawings.

DESCRIPTION

The detailed description provided below in connection with the appended drawings is intended to describe the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples, and appended claims are collected here. Unless otherwise defined herein, scientific and technical terminologies employed in the present disclosure shall have meanings commonly understood and used by one of ordinary skill in the art.

Unless otherwise required by context, it will be understood that singular terms shall include plural forms of the same, and plural terms shall include the singular. Also, as used herein and in the claims, the terms "at least one" and "one or more" have the same meaning and include one, two, three, or more. Furthermore, the phrases "at least one of A, B, and C," "at least one of A, B, or C," and "at least one of A, B and/or C" used throughout this specification and the appended claims, are intended to cover A alone, B alone, C alone, A and B together, B and C together, A and C together, as well as A, B, and C together.

Notwithstanding that the numerical ranges and parameters setting forth the broad scope of the invention are approximations, the numerical values outlined in the specific examples are reported as precisely as possible. However, any numerical value inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values, and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters outlined in the present disclosure and attached claims are approximations that can vary as desired. At the very least, each numerical parameter should at least be construed in light of the number of reported significant digits and by applying ordinary rounding techniques. Ranges can be expressed herein as from one endpoint to another endpoint or between two endpoints. All ranges disclosed herein are inclusive of the endpoint unless specified otherwise.

The term "degree of substitution (DS)" of the HA conjugate, as used herein, is the average ratio of substituent groups (i.e., the sex hormone) attached per disaccharide unit of the HA.

As used herein, the term "salt" refers to any and all salts and encompasses pharmaceutically acceptable salts. The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art.

As used herein, the term "linker" means a chemical moiety (e.g., a chemical bond form between two functional groups) that connects two parts of a conjugate. The linker may be any chemical moiety present between the drug molecule and the hyaluronan molecule in the present disclosure. In some embodiments of the present disclosure, the linker may be digested chemically or enzymatically; alternatively, it may degrade spontaneously.

Conventionally, the DIC/Oxyma coupling system has been used in heterogeneous reaction phases, such as solid-phase peptide synthesis. As DIC is not soluble in water, DIC cannot work in an aqueous reaction system. On the other hand, the synthesis of HA-drug conjugates is carried out in the aqueous phase. Hence, only coupling systems compatible with the aqueous reaction phase (e.g., the EDC/NHS coupling system) can be used in synthesizing HA-drug conjugates. In contrast, the conventional DIC/Oxyma coupling system is incompatible with the conventional HA-drug conjugates synthesis process.

The present disclosure is based, at least in part, on an unexpected discovery that using a co-solvent (e.g., DMSO) allows the DIC/oxyma coupling system to work in a homogenous reaction system that is relatively aqueous. As a consequence, the DIC/oxyma coupling system successfully allows for the coupling between the hyaluronan molecule and the drug molecule. Using the DIC/Oxyma coupling system avoids the re-arrangement issue that is often experienced when using the conventional EDC/NHS coupling system for synthesizing HA-drug conjugates, thereby improving the substitution rate as well as the substitution efficiency of HA-drug conjugates.

According to various embodiments of the present disclosure, the method for synthesizing a hyaluronan-drug conjugate comprises the following steps: preparing a drug solution by dissolving a plurality of drug molecules in DMSO; preparing an additive solution by dissolving an additive in DMSO; preparing a hyaluronan solution by dissolving a plurality of hyaluronan molecules in distilled water and DMSO; mixing the drug solution, the additive solution, the hyaluronan solution and DIC to obtain a reaction mixture; and allowing components in the reaction mixture to react, thereby forming the hyaluronan-drug conjugate.

According to the present disclosure's embodiments, each of the above-mentioned drug solution, coupling solution, additive solution, and hyaluronan solution comprises DMSO as a co-solvent. However, the present disclosure is not limited thereto; instead, other organic solvents can be used, as long as a similar technical purpose (that is, allowing the DIC/oxyma coupling system to work in a reaction system suitable for the synthesis of HA-drug conjugates) can be achieved.

According to optional embodiments of the present disclosure, at least one of the drug molecules has or is modified to have an amino group. In some embodiments, the amino group is a primary amine. In some embodiments, the at least one drug molecule is modified with a linker, wherein the linker is one or more amino acids (e.g., β-alanine (β-Ala) or glycine) or urea. As could be appreciated, in some optional embodiments, when the drug molecule has an original amino group, it may be advantageous to modify such drug molecule so that it has an amino group that is more reactive (e.g., a primary amino group).

In some embodiments, the linker is a single amino acid residue, such as alanine (Ala; preferably, β-alanine), arginine (Arg), asparagine (Asn), aspartic acid (Asp), cysteine (Cys), glutamic acid (Glu), glutamine (Gln), glycine (Gly), histidine (His), isoleucine (Ilu), leucine (Leu), lysine (Lys), methionine (Met), phenylalanine (Phe), proline (Pro), serine (Ser), threonine (Thr), tryptophan (Trp), tyrosine (Tyr), valine (Val), γ-abu (4-aminobutanoic acid), δ-aminovaleric acid (5-aminopentanoic acid), ε-aminocaproic acid (6-aminohexanoic acid), 7-aminoheptanoic acid, 8-aminooctanoic acid, and 11-aminoundecanoic acid. In some embodiments, the linker may be a short peptide having two to 100 amino acid residues. For example, the linker may be a flexible peptide with a sequence of $(G_nS)_m$, where n and m are independently a number between 1 and 4.

As could be appreciated, when at least one of the drug molecules is modified to have a primary amine, it is preferable to activate the HA before adding the drug solution to improve the degree of substitution and/or substitution efficiency. In some optional embodiments of the present disclosure, the step of mixing the drug solution, the additive solution, the hyaluronan solution and DIC comprises the steps of, preparing a hyaluronan/additive solution by adding the additive solution into the hyaluronan solution; adding the drug solution into the hyaluronan/additive solution; and adding DIC into the hyaluronan/additive solution.

According to embodiments of in the present disclosure, DIC is used as the coupling agent for the conjugation between the HA and the drug (or the drug-linker) with at least one amino group. However, the carbodiimide activation of amino acid derivatives often causes a partial racemization of the amino acid. Therefore, when choosing the additive, it is preferred that the additive is capable of reducing the carbodiimide-related racemization to an insignificant level. For example, the additive can be Oxyma, HOBt, or NHS.

According to some other optional embodiments of the present disclosure, at least one of the drug molecules has or is modified to have a carboxylate group. In some embodiments, the drug molecule is modified with a $C_2$-$C_{20}$ dicarboxylic acid (e.g., succinic acid). Illustrative examples of the $C_2$-$C_{20}$ dicarboxylic acid may be oxalic acid, malonic acid, succinic acid, glutaric acid, adipic acid, pimelic acid, suberic acid, azelaic acid, sebacic acid, dodecanedioic acid, brassylic acid, thapsic acid, diabolic acids, crocetin, maleic acid, fumaric acid, glutaconic acid, 2-decenedioic acid, traumatic acid, muconic acid, glutinic acid, citraconic acid, mesaconic acid, itaconic acid, tartronic acid, mesoxalic acid, malic acid, tartaric acid, oxaloacetic acid, aspartic acid, α-hydroxyglutaric acid, arabinaric acid, acetonedicarboxylic acid, α-ketoglutaric acid, glutamic acid, diaminopimelic acid, saccharic acid, phthalic acid, isophthalic acid, terephthalic acid, diphenic acid, or 2,6-naphthalenedicarboxylic acid.

In some optional embodiments, at least one of the plurality of hyaluronan molecules is modified with a linker, such as a dihydrazide (e.g., adipic acid dihydrazide (ADH)). A dihydrazide linker includes, but is not limited to adipic acid dihydrazide (ADH), sebacic acid dihydrazide (SDH), valine dihydrazide (VDH), isophthalic dihydrazide (IDH), carbodihydrazide (CDH), icosanedioic acid dihydrazide (LDH), succinic dihydrazide, adipic dihydrazide, dihydrazide sulfoxide, oxalic dihydrazide, and pimelic acid dihydrazide.

In still some embodiments, the $C_2$-$C_{20}$ dicarboxylic acid-modified drug molecules can be coupled to the dihydrazide-modified hyaluronan molecules.

According to some embodiments of the present disclosure, the HA of the present hyaluronan conjugate has a weight-average molecular weight (Mw) ranging from about 5 kDa to about 500 kDa, for example, about 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 kDa.

According to some embodiments of the present disclosure, the HA of the present hyaluronan conjugate may be in an unsubstituted (i.e., the HA per se) or a substituted (i.e., the HA derivative) form, or a salt thereof. As described above, HA can be modified on its functional groups such as hydroxyl, carboxyl, amide, or acetylamino groups. HA can be modified by esterification, grafting, and/or hydrophobization on its functional groups (i.e., hydroxyl, carboxyl, amide, or acetylamino groups) as described above through reaction with a series of chemical agents. Exemplary HA derivatives are ethylsulfonated HA, deacetylated HA, or hydrazide-modified HA. In one example of the present disclosure, the HA of the present hyaluronan conjugate is in an unsubstituted form. In another example of the present disclosure, the HA of the present hyaluronan conjugate is in a substituted form.

According to various embodiments of the present disclosure, the present HA-drug conjugate has a degree of substitution (DS) with the drug molecule of 0.5 to 70%. According to working examples of the present disclosure, the degree of substitution is determined using the H-NMR spectrum. For example, the DS may be 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69 or 70%.

According to some other optional embodiments of the present disclosure, the HA-drug conjugate has a substitution efficiency of at least 20%. In the present disclosure, the substitution efficiency is defined as: Substitution Efficiency=DS/Reaction Equivalent of the Drug. For example, the substitution efficiency may be 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%.

According to various embodiments of the present disclosure, the drug molecule is a steroid drug, nucleoside or nucleotide analog, non-steroid anti-inflammatory drug (NSAID), a cytotoxic drug, or immunomodulator.

For example, the steroid drug is cholesterol, cortisone, hydrocortisone, prednisolone, methylprednisolone, dehydroepiandrosterone, triamcinolone, dexamethasone, betamethasone, triamcinolone acetonide, or budesonide. In some other embodiments, the steroid can be a sex hormone, such as estrone, estradiol, estriol, testosterone, or 11-deoxycorticosterone.

Non-limiting examples of the nucleoside or nucleotide analog include deoxyadenosine analogs, adenosine analogs, deoxycytidine analogs, guanosine analogs, deoxyguanosine analogs, thymidine analogs, deoxythymidine analogs, and deoxyuridine analogs. For example, the nucleoside or nucleotide analogs can be didanosine, vidarabine, galidesivir, remdesivir, cytarabine, gemcitabine, emtricitabine, lamivudine, zalcitabine, abacavir, acyclovir, entecavir, stavudine, telbivudine, azidothymidine, idoxuridine, or trifluridine.

Illustrative examples of NSAID include, but are not limited to, aspirin, ibuprofen, nimesulide, diclofenac, mefenamic acid, naproxen, sulindac, ketorolac, ketoprofen, tenoxicam, indomethacin, valdecoxib, celecoxib, etoricoxib, and rofecoxib. Cytotoxic drugs can be, such as azacytidine, belinostat, bendamustine, brentuximab vedotin, bleomycin, bortezomib, busulfan, carboplatin, carmustine, cyclophosphamide, cytarabine, dacarbazine, dactinomycin, daunorubicin, decitabine, deferoxamine, doxorubicin, epirubicin hydrochloride, fludarabine, fotemustine, fulvestrant, gemcitabine, idarubicin, ifosfamide, irinotecan hydrochloride, ixabepilone, melphalan, methotrexate, oxaliplatin, paclitaxel, pemetrexed, pentostatin, raltitrexed, romidepsin, temozolomide, thiotepa, topotecan, trabectedin, trastuzumab, or vinblastine.

Examples of immunomodulators include, but are not limited to, lenalidomide, pomalidomide and thalidomide.

The following Examples are provided to elucidate certain aspects of the present invention and aid those skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLES

Comparative Examples

In the following comparative examples, HA was conjugated with various drugs using conventional coupling systems such as PyBOP, EDC/NHS, or DIC/HOBt.

(1) Synthesis of HA-ADH-Prednisolone-Hemisuccinate

For synthesizing HA-ADH, 4,000 mg of 360K HA (10.55 mmol) and 9,200 mg of ADH (52.81 mmol) were added to 1,000 mL of double distilled water (DDW) under ultrasonic vibration and stirring until dissolved completely; then, the pH of the HA/ADH solution was adjusted to 4.75 using 0.1 M HCl aqueous solution. 2,040 mg of EDC (13.14 mmol) was added to the HA/ADH solution, and the solution was allowed to stand for 15 minutes under room temperature, during which period, the acidity is monitored and maintained at pH 4.75 by adding HCl aqueous solution. Then, 0.1 M NaOH aqueous solution was added to adjust the pH to 7.00. The steps mentioned above were repeated once, and the final product solution of 2 liters was obtained. The product solution was dialyzed using a 3,500 MWCO dialysis bag with 10 L DDW dialysis, 10 L 0.3 M NaCl, and 10 L DDW×4 times (replaced thrice daily); the retenant was freeze-dried (DS=32.4%).

For synthesizing HA-ADH-prednisolone-hemisuccinate using EDC/NHS, 1,000 mg of 360K HA-ADH (DS=32.4%) was added to a solution containing 70 ml DMSO and 100 ml DDW under ultrasonic vibration and stirring until dissolved completely; then, the reaction mixture was placed in the oil bath for 30 minutes for temperature balance with the temperature of the outer pot being 35° C. (Bottle A). 1,137.0 mg of sodium prednisolone-hemisuccinate (3.1 eq), 282.6 mg of NHS, and 550.0 mg of EDC-HCl were dissolved in 30 ml DMSO; the reaction mixture was allowed to react until it turned transparent from pale yellow (Bottle B). The Bottle B was added to Bottle A, and the reaction mixture was allowed to stand for 48 hours with an outer pot of 35° C. The steps mentioned above were repeated twice, and the reaction solutions were mixed with stirring for 5 minutes. The product solution was dialyzed using a 3,500 MWCO dialysis bag with 10 L DDW dialysis (one day), 10 L 0.3 M NaCl×2 times (one day), and 10 L DDW×5 times (replaced thrice daily); the retenant was freeze-dried. The degree of substitution was determined using $^1$H-NMR spectrum, and the HA-ADH-prednisolone-hemisuccinate using EDC/NHS as the coupling system has a DS of 8.43%. The substitution efficiency is 8.3% (substitution efficiency=DS/equivalent of the drug).

For synthesizing HA-ADH-prednisolone-hemisuccinate using DIC/HOBt, 497.8 mg of 360K HA-ADH (DS=32.4%) was added to a solution containing 70 ml DMSO and 100 ml DDW under ultrasonic vibration and stirring until dissolved completely; then, the reaction mixture was allowed to stand until it reached room temperature (Bottle A). 570.4 mg of sodium prednisolone-hemisuccinate (3.2 eq) and 188.0 mg of HOBt were dissolved in 30 ml DMSO under stirring until completely dissolved; then, 223 µL DIC (180 mg, 1.42 mmol) was added therein with the tip under the level. The reaction mixture was allowed to react for 15 minutes (Bottle B). Bottle B was added to Bottle A, and the reaction mixture was allowed to stand for 24 hours at room temperature. The product solution was dialyzed using a 3,500 MWCO dialysis bag with 10 L DDW dialysis, 10 L 0.3 M NaCl, and 10 L DDW×5 times (replaced twice daily); the retenant was freeze-dried (DS=0.6%).

(2) Synthesis of HA-Nimesulide

For synthesizing HA-Nimesulide using EDC/NHS, 1,000 mg of 360K HA was dissolved in 450 mL DDW; 552.2 mg of EDC (1.1 eq)/302 mg of NHS (1 eq) were dissolved in 20 ml DDW and then added to the HA solution to activate the HA for 5 minutes. 79.2 mg of NiNH$_2$ (0.11 eq) was dissolved in 22 mL DMSO and then added to the HA solution dropwisely; the reaction mixture was allowed to stand for 24 hours. The product solution was dialyzed, and the DS as determined by the $^1$H-NMR spectrum is 1.1%; the substitution efficiency is 10%.

For synthesizing HA-Nimesulide using DIC/HOBt, 100 mg of 360K HA was dissolved in 10 ml DDW; 15 mL DMSO was added to the HA solution; then, 30 mg of HOBt (0.8 eq) was dissolved in 1 mL DMSO and then added to the HA solution. The solution was stirred for 6 minutes. 2.2 mg (0.031 eq), 5.1 mg (0.074 eq), 10.1 mg (0.146 eq), 17.5 mg (0.25 eq), or 26.4 mg (0.38 eq) of NiNH$_2$ was dissolved in 1 mL DMSO and then added to the HA solution dropwisely and stirred for 1 minute; then, 81 µl DIC (2 eq) was added therein with the tip under the level. The reaction mixture was allowed to stand for 24 hours. The product solution was dialyzed, and the DS as determined by the $^1$H-NMR spectrum and the substitution efficiency are summarized in Table 1. Linear regression showed that the relationship between the DS and the drug amount is linear with $R^2=0.9982$.

TABLE 1

| Amount of $NiNH_2$ (in eq) | DS (%) | Substitution efficiency (%) |
|---|---|---|
| 0.031 | 2.36 | 76 |
| 0.074 | 4.15 | 56 |
| 0.146 | 9.01 | 61.7 |
| 0.25 | 14.74 | 59.0 |
| 0.38 | 22.99 | 60.5 |

PyBOP is used in all-organic phase synthesis; hence, for synthesizing HA-Nimesulide using PyBOP, quaternary ammonium salts of HA was first prepared. First, free form HA was obtained as follows: dissolving 360 kDa HA-sodium salt in DDW (5 mg/mL); washing Dowex 50WX-8 ion exchange resins with 500 ml DDW under stirred and filtrating it thrice to replace the sodium ions with hydrogen ions; slowly adding resins into the HA solution with continuous stirring under pH monitoring until the pH was lowered to 2.5; filtering the resins and freeze-drying the filtrate to obtain free form HA. 50 mg of free form HA was dissolved in 1 ml DDW, 20 mg (58%) of TBA-OH (40 w/w %) was added to the HA solution, and the reaction mixture was stirred for 4 hours and then freeze-dried to obtain white blocks. 15 mg of 360 kDa HA-TBA was dissolved in NMP and DMSO, 9.4 mg of $NiNH_2$ (1.34 eq) and 16.6 mg of PyBOP 16.6 were added to the HA-TBA solution, and the reaction mixture was allowed to react for 24 hours. The product solution was dialyzed using a dialysis bag with MWCO 12000~14000 (DS: 4.6%; substitution efficiency: 3.4%).

(3) Synthesis of HA-Lenalidomide

For synthesizing HA-Lenalidomide using EDC/NHS, 161 mg of 360K HA was dissolved in 30 mL DDW and 15 mL DMSO; 78 mg of EDC (1 eq) and 47 mg of NHS (1 eq) were dissolved in 3 ml DDW and then immediately added to the HA solution to activate the HA for 5 minutes. 82.1 mg of $NiNH_2$ (0.79 eq) was dissolved in 22 mL DMSO and then added to the HA/EDC/NHS solution slowly; the reaction mixture was allowed to stand for 12 hours. The product solution was dialyzed, and the DS as determined by the $^2$H-NMR spectrum is 2%; the substitution efficiency is 2.5%.

For synthesizing HA-Lenalidomide using DIC/HOBt, 1,000 mg of 360K HA was dissolved in 100 ml DDW; 80 mL DMSO was added to the HA solution until the HA dissolves completely; 100 mg of HOBt (0.26 eq) was dissolved in 10 ml DMSO and 117.1 mg of lenalidomide (0.18 eq) was dissolved in 10 ml DMSO; the HOBt solution and the lenalidomide solution were then added to the HA solution and mixed well; 810 µl DIC (2 eq) was added therein with the tip under the level. The reaction mixture was allowed to stand for 24 hours. The product solution was dialyzed; the DS is 1.77%, and the substitution efficiency is 9.8%.

For synthesizing HA-Lenalidomide using PyBOP, 50.8 mg of free form HA (47 kDa) was dissolved in 5 mL DDW; next, 5 ml DMSO was added to the HA solution; then 13.8 mg of lenalidomide (0.626 eq), and 15 mg (20.7 ml) of triethylamine (TEA) was added to the HA solution, and then 76 mg of PyBOP were added therein, and the reaction mixture was allowed to react for 24 hours at room temperature. The product solution was dialyzed using a dialysis bag with MWCO 3500, and the analysis showed no lenalidomide conjugated onto the HA (DS: 0%).

(4) Synthesis of HA-β-Ala-Gemcitabine

First, Boc-β-alanine-gemcitabine was prepared. Briefly, gemcitabine (200 mg) was dissolved in DMF (2 ml), and then, EDCl (192 mg) and HOBt (135.13 mg) were added. The reaction mixture was stirred at room temperature under the nitrogen atmosphere for 30 minutes. After that, Boc-β-Ala-OH (192 mg) was added, and the reaction mixture was stirred at room temperature under the nitrogen atmosphere. Then, the solvent was evaporated using a rotavapour. The product was then purified by silica gel column chromatography (eluent: DCM:MeOH=10:1) to obtain the product, Boc-β-Ala-gemcitabine (yield: 80%).

For synthesizing HA-β-Ala-Gemcitabine using EDC/NHS, 30 mg of 360K HA (0.0746 mmol, 1 eq) was dissolved in DDW and DMSO; 17.16 mg of EDC (1.2 eq) and 10.3 mg of NHS (1.2 eq) were dissolved in DDW and then added to the HA solution. 3.24 mg of Gem-β-Ala-Boc (0.1 eq) was de-protected and then dissolved in DMSO, which was then added to the HA/EDC/NHS solution slowly; the reaction mixture was allowed to react. The product solution was dialyzed, and the DS as determined by the $^1$H-NMR spectrum is 0.97%; the substitution efficiency is 9.7%.

For synthesizing HA-β-Ala-Gemcitabine using DIC/HOBt, 30 mg of 360K HA (0.0746 mmol, 1 eq) was dissolved in DDW; then DMSO was added to the HA solution until the HA dissolves completely; 12.1 mg of HOBt (1.2 eq) was dissolved in DMSO, and 3.24 mg of Gem-β-Ala-Boc (0.1 eq) was de-protected and then dissolved in DMSO; the HOBt solution and the Gem-β-Ala solution were then added to the HA solution and mixed well; 14 µL DIC (1.2 eq) was added therein with the tip under the level. The reaction mixture was allowed to react. The product solution was dialyzed; the DS is 2.88%, and the substitution efficiency is 28%.

For synthesizing HA-β-Ala-Gemcitabine using PyBOP, 30 mg of 360K HA (0.0746 mmol, 1 eq) was dissolved in DDW; next, DMSO was added to the HA solution; then 3.24 mg of Gem-β-Ala-Boc (0.1 eq) was de-protected and then added to the HA solution, and then 42.71 mg of PyBOP (1.1 eq) was added therein. The reaction mixture was allowed to react. The product solution was dialyzed, and the analysis showed no Gem-β-Ala conjugated onto the HA (DS: 0%).

(5) Synthesis of HA-β-Ala-Estradiol

First, Boc-β-alanine-estradiol was prepared. Briefly, Boc-β-alanine (2.92 mmol, 552 mg), DCC (3.40 mmol, 702 mg), and 4-dimethylaminopyridine (DMAP) (3.04 mmol, 372 mg) were added to a solution of estradiol (2.75 mmol, 750 mg) in dichloromethane (DCM) (250 mL), and the mixture was stirred overnight at room temperature. The solvent was removed under vacuum, and the precipitate was then dissolved by methanol. The resulting mixture was added with 10% $K_2CO_3$ solution (methanol:10% $K_2CO_3$=1:1) and stirred overnight at room temperature. Then, the mixture was concentrated and extracted by DCM and water. Most DCM within the mixture was removed under vacuum, and the precipitate within the mixture was filtered out. The filtrate was washed by DCM and concentrated under vacuum. The residue was washed with acetone, and the precipitate was filtered out. After that, the filtrate was concentrated and then purified by silica gel column chromatography (eluent: acetone:hexane=1:1) to obtain the product, Boc-β-Ala-E2.

For synthesizing HA-β-Ala-E2 using EDC/NHS, 30 mg of 360K HA (0.0746 mmol, 1 eq) was dissolved in DDW and DMSO; 17.16 mg of EDC (1.2 eq) and 10.3 mg of NHS (1.2 eq) were dissolved in DDW and then added to the HA solution. 443.58 mg of E2-β-Ala-Boc (0.1 eq) was de-protected and then dissolved in DMSO, which was then added to the HA/EDC/NHS solution slowly; the reaction mixture was allowed to react. The product solution was dialyzed, and the DS as determined by the $^1$H-NMR spectrum is 2.75%; the substitution efficiency is 27.5%.

For synthesizing HA-β-Ala-Gemcitabine using DIC/HOBt, 30 mg of 360K HA (0.0746 mmol, 1 eq) was dissolved in DDW; then DMSO was added to the HA solution until the HA dissolves completely; 12.1 mg of HOBt (1.2 eq) was dissolved in DMSO, and 443.58 mg of E2-β-Ala-Boc (0.1 eq) was de-protected and then dissolved in DMSO; the HOBt solution and the Gem-β-Ala solution were then added to the HA solution and mixed well; 14 μL DIC (1.2 eq) was added therein with the tip under the level. The reaction mixture was allowed to react. The product solution was dialyzed, and the DS as determined by the $^1$H-NMR spectrum is 8.02%; the substitution efficiency is 80.2%.

For synthesizing HA-β-Ala-Gemcitabine using PyBOP, 30 mg of 360K HA (0.0746 mmol, 1 eq) was dissolved in DDW; next, DMSO was added to the HA solution; then 443.58 mg of E2-β-Ala-Boc (0.1 eq) was de-protected and then added to the HA solution, and then 42.71 mg of PyBOP (1.1 eq) was added therein. The reaction mixture was allowed to react. The product solution was dialyzed, and the DS as determined by the $^2$H-NMR spectrum is 0.6%; the substitution efficiency is 6%.

Example 1

Synthesis of HA-ADH-Prednisolone-Hemisuccinate and HA-ADH-Prednisolone

For synthesizing HA-ADH-prednisolone-hemisuccinate using DIC/Oxyma, 497.8 mg of 360K HA-ADH (DS=32.4%) was added to a solution containing 70 ml DMSO and 100 ml DDW under ultrasonic vibration and stirring until dissolved completely; then, the reaction mixture was allowed to stand until it reached room temperature (Bottle A). 570.4 mg of sodium prednisolone-hemisuccinate (3.2 eq) and 175 mg of Oxyma were dissolved in 30 ml DMSO under stirring until completely dissolved; then, 223 μl DIC (180 mg, 1.42 mmol) was added therein with the tip under the level. The reaction mixture was allowed to react for 15 minutes (Bottle B). Bottle B was added to Bottle A, and the reaction mixture was allowed to stand for 24 hours at room temperature. The product solution was dialyzed using a 3,500 MWCO dialysis bag with 10 L DDW dialysis, 10 L 0.3 M NaCl, and 10 L DDW×5 times (replaced twice daily); the retenant was freeze-dried (DS=0.52%).

For synthesizing HA-β-Ala-prednisolone using DIC/Oxyma, the boc protection group on Pred-β-Ala-Boc was first removed by dissolving 100 mg of Pred-β-Ala-Boc in 1 mL DCM; then, adding 1 mL TFA; the mixture was allowed to react for 3 hours under the monitoring of TLC (hexane:acetone 1:1) to confirm the completion of the reaction. Then, an ice sodium bicarbonate aqueous solution (1.1 g of NaHCO$_3$ in 20 g of iced water) was prepared, and the product in the de-boc reaction bottle was slowly added to the ice sodium bicarbonate aqueous solution in an ice bath dropwisely; 5 mL DMSO was added to the solution for further use until no bubble was generated (Bottle A). 500 mg of HA was added to 25 ml DDW, and after the HA dissolved completely, 35 ml DMSO was added to the HA solution under stirring, and the reaction mixture was allowed to reached room temperature (Bottle B). Then, 220 mg of Oxyma and Bottle A were added to Bottle B, and the mixture was stirred until homogenous. Then, 405 μl DIC was slowly added therein with the tip under the level. The reaction mixture was allowed to react for 24 hours. The product solution was dialyzed and then freeze-dried (DS=43.4%).

The data in this working example indicates that using the present DIC/Oxyma conjugation system in connection with the Ala linker significantly increases the degree of substitution, compared with conventional approaches (see comparative examples above).

Example 2

Synthesis of HA-Nimesulide and HA4-Nimesulide

For synthesizing HA-Nimesulide using DIC/Oxyma or DIC/HOBt, 100 mg of 360K HA was dissolved in 8 ml DDW; 12 ml DMSO was added to the HA solution; then, 9.3 mg (0.26 eq) or 28.3 mg (0.8 eq) of DIC or 10 mg HOBt (0.26 eq) was first dissolved in 1 ml DMSO and then mixed with 81 μL DIC (2 eq) and then added to the HA solution to activate the HA for three minutes. 12 mg (0.173 eq) of NiNH$_2$ was dissolved in 1 ml DMSO and then added to the HA solution dropwisely. The reaction mixture was allowed to stand for 24 hours. The product solution was dialyzed, and the DS as determined by the $^1$H-NMR spectrum and the substitution efficiency are summarized in Table 2.

TABLE 2

| Coupling System | DS (%) | Substitution efficiency (%) |
| --- | --- | --- |
| DIC/HOBt (0.26 eq) | 6.76 | 39.0 |
| DIC/Oxyma (0.26 eq) | 14.15 | 81.8 |
| DIC/Oxyma (0.8 eq) | 16.87 | 91.3 |

The data shown in Table 2, when considered in connection with Table 1, show that the present DIC/Oxyma coupling system significantly improves the degree of substitution and substitution efficiency of HA-Nimesulide conjugates, compared with conventional coupling systems such as DIC/HOBt.

For synthesizing tetra-saccharide HA (HA4)-nimesulide was first prepared for synthesizing HA4-Nimesulide. Briefly, 50 mg of HA4 (0.06437 mmol) was dissolved in 3 mL DDW; then, 5 mL DMSO was added to the HA4 solution. 9.1 mg of Oxyma (0.06437 mmol) was dissolved in 0.5 mL DMSO and then added to the HA4 solution under stirring for 6 minutes; then, the 17.9 mg of nimesulide-Boc (0.07081 mmol) was de-protected and then dissolved in 0.5 ml DMSO and added to the HA4 solution. 14 μL DIC (0.09656 mmol) was dissolved in 0.5 mL DMSO under stirring for 1 minute and then added to the HA4 solution. The final reaction mixture was stirred for 48 hours at room temperature, and the resulting solution was freeze dryer for three days and purified by RP-TLC (Merck, 1.05559.0001). The thus-synthesized HA4-Nimesulide has the following structures:

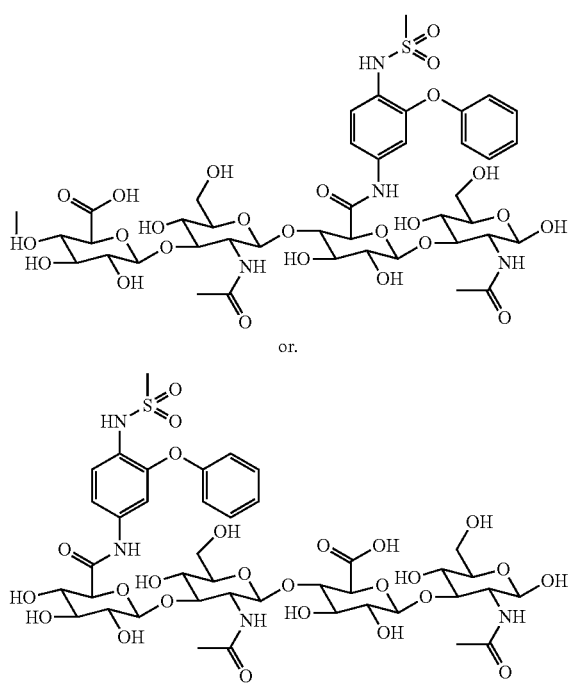

Example 3

Synthesis of HA-Lenalidomide and HA-β-Ala-Lenalidomide

For synthesizing HA-Lenalidomide, 200 mg of 210K HA (0.4975 mmol) was dissolved in 20 ml DDW; then 35 ml DMSO was added to the HA solution under stirring until it reached room temperature. 70 mg of Oxyma (0.4975 mmol) was dissolved in 3 mL DMSO and added to the HA solution, and the mixture was stirred for 6 minutes. Then, 50 mg of lenalidomide (0.1940 mmol) was dissolved in 3 mL DMSO and added to the HA solution. 160 µL DIC (0.9950 mmol) was dissolved in 3 ml DMSO and added to the HA solution. The final reaction mixture was stirred for 24 hours at room temperature, and the resulting solution was dialyzed using 0.3M Nacl solutions for four days and then freeze-dried for three days (DS=8.5%).

To investigate the relationship between the degree of substitution and drug equivalent, HA was reacted conjugated with different equivalents of lenalidomide. Briefly, 100.0 mg of 190K HA (0.25 mmol) was dissolved in 10 mL DDW then 15 ml DMSO was added to the HA solution. 35.3 mg of Oxyma (0.25 mmol) was dissolved in 1 ml DMSO and added to the HA solution. Then, 25.2 mg (0.097 mmol; 0.39 eq), 42.6 mg (0.16 mmol; 0.66 eq), or 64.5 mg (0.25 mmol; 1.00 eq) of lenalidomide was dissolved in 3 mL DMSO and added to the HA solution. 77.8 µL DIC (0.5 mmol) was dissolved in 3 ml DMSO and added to the HA solution. The final reaction mixture was stirred for 24 hours at room temperature, and the resulting solution was dialyzed. The DS as determined by the $^1$H-NMR spectrum and the substitution efficiency are summarized in Table 3. The data in Table 3 indicate that the degree of substation for HA-Lenalidomide DS conjugates relates positively to the amount of lenalidomide used during the conjugation reaction. Linear regression showed that the relationship between the DS and the drug amount is linear with $R^2$=0.9964.

TABLE 3

| Amount of Lenalidomide (in eq) | DS (%) | Substitution efficiency (%) |
|---|---|---|
| 0.39 | 5.71 | 14.64 |
| 0.66 | 9.64 | 14.61 |
| 1.00 | 13.66 | 13.66 |

In another example, 500 mg of 190K HA (1.2438 mmol) was dissolved in 50 mL DDW then 86 ml DMSO was added to the HA solution after the HA dissolved. 176.6 mg of Oxyma (1.2438 mmol) was dissolved in 5 mL DMSO and added to the HA solution. Then, 234.6 mg of lenalidomide (0.72767 mmol) was dissolved in 5 mL DMSO and added to the HA solution. 388.9 µl DIC (2.4876 mmol) was added to the HA solution. The final reaction mixture was stirred for 24 hours at room temperature, and the resulting solution was dialyzed (DS=14.94%).

Lenalidomide-β-Ala-Boc was first prepared in order to synthesize HA-β-Ala-Lenalidomide. Briefly, Boc-β-Ala-OH (803.0 mg, 4.24 mmol) was dissolved in DMF (5 mL), EDC/HCl (812.8 mg, 4.24 mmol), and HOBt (573.3 mg, 4.24 mmol) was added to the Boc-β-Ala-OH solution. The reaction mixture was stirred at 65° C. under the $N_2$ atmosphere for 30 minutes. 1000.0 mg of Lenalidomide (3.86 mmol) was added, and the reaction mixture was stirred for 24 hours at room temperature under the $N_2$ atmosphere. The solvent was then evaporated using a rotavapor. The product was isolated using the silica gel packed column with DCM/MeOH (96:4) as an eluent. The Lenalidomide-β-Ala-Boc white solid yield was 24% (400 mg), and the structure was confirmed by $^1$H NMR. Lenalidomide-β-Ala-Boc was de-protected before being conjugated with the HA to obtain lenalidomide-β-Ala-$NH_2$.

For synthesizing HA-β-Ala-Lenalidomide, 210K HA (500.0 mg, 1.2439 mmol) was dissolved in 50 mL of DDW. Next, 75 ml DMSO was added to the HA solution. Then, Oxyma (194.0 mg, 1.3681 mmol) was dissolved in 5 mL DMSO and added to the HA solution; then, the reaction mixture was stirred for 6 minutes. 48.0 mg of lenalidomide-β-Ala-Boc (0.1119 mmol) was de-protected and then dissolved in 5 mL DMSO and then added to the HA solution; then, the reaction mixture was stirred for 1 minute. Next, 386 µL DIC (2.4875 mmol) was dissolved in 5 ml DMSO and then added to the HA solution; the reaction mixture was stirred for 24 hours at room temperature; the resulting solution was dialyzed for two days using 0.3 M NaCl solution and two days using DDW and freeze-dried for three days. The DS as determined by the $^1$H-NMR spectrum is 9.27%.

Example 4

Synthesis of HA-Gemcitabine and HA-β-Ala-Gemcitabine

For synthesizing HA-Gem, 500 mg of 360K HA (1.2439 mmol) was dissolved in 50 ml DDW; then, 75 mL DMSO was added to the HA solution. 194.0 mg of Oxyma (1.3681 mmol) was dissolved in 5 ml DMSO and then added to the HA solution, and the reaction mixture was stirred for 6 minutes. Next, 327.3 mg of gemcitabine (1.2437 mmol) was dissolved in 5 mL water and then added to the HA solution. After stirring 1 min, (386 µl, 2.4875 mmol) of DIC was dissolved in 5 mL DMSO added to HA solution. The reaction mixture was stirred for 24 hours at room temperature. The resulting solution was dialyzed using 0.3 M NaCl solution for four days and then freeze-dried for three days. The DS as determined by the $^1$H-NMR spectrum is 1.15%.

Gemcitabine-β-Ala-Boc was first prepared in order to synthesize HA-β-Ala-Gem. Briefly, 863 mg of Boc-β-Alanine (4.56 mmol) was dissolved in 5 mL dry DMF. Nitrogen gas was purged to remove air. 648 mg of Oxyma (4.56 mmol) was dissolved in 2.5 mL dry DMF and then added to the Boc-β-Ala solution. After that, 1,000 mg of gemcitabine (3.8 mmol) was dissolved in 5 ml dry DMF and then added to the reaction mixture. Finally, 575 mg of DIC (4.56 mmol) dissolved in 2.5 ml dry DMF was added using a syringe pump over 2 hours (flow rate: 1.25 mL/hr). The reaction mixture was allowed to react 24 hours under a nitrogen environment at room temperature. Afterward, Gem-β-Ala-Boc was extracted into the ethyl acetate (EA) layer using cold salt water and EA. Then, a concentrated crude product was obtained by evaporating EA using a rotavapor. Finally, the crude product was subjected to a silica gel column (DCM-70%, EA-25%, MeOH-5%) to separate Gem-β-Ala-Boc from impurities (yield: 22%).

For synthesizing HA-β-Ala-Gem, 100.0 mg of 360K HA was dissolved in 10 ml of DDW. Next, 15 ml DMSO was added to the HA solution. Then, 36 mg of Oxyma was dissolved in 1 ml DMSO and added to the HA solution; then, the reaction mixture was stirred for 6 minutes. 20, 40, or 60 mg of gemcitabine-β-Ala-NH$_2$ was dissolved in 1 ml DMSO and then added to the HA solution; then, the reaction mixture was stirred for 1 minute. Next, 81 μL DIC was dissolved in 1 mL DMSO and then added to the HA solution; the reaction mixture was stirred for 24 hours at room temperature; the resulting solution was dialyzed for four days, and then freeze-dried for three days. The DS as determined by the $^1$H-NMR spectrum is 5.83% (20 mg gemcitabine), 7.84% (40 mg gemcitabine), or 8.67% (60 mg gemcitabine).

Example 5

Synthesis of HA-β-Ala-Estradiol

For synthesizing HA-β-Ala-Estradiol, 500.0 mg of 360K HA (1.2439 mmol) was dissolved in 50 ml of DDW. Next, 75 ml DMSO was added to the HA solution. Then, 194.0 mg of Oxyma (1.3681 mmol) was dissolved in 5 ml DMSO and added to the HA solution; then, the reaction mixture was stirred for 6 minutes. 110.3 mg of estradiol-β-Ala-NH$_2$ (0.2487 mmol) was dissolved in 5 ml DMSO and then added to the HA solution; then, the reaction mixture was stirred for 1 minute. Next, 386 μL DIC (2.4875 mmol) was dissolved in 5 ml DMSO and then added to the HA solution; the reaction mixture was stirred for 24 hours at room temperature; the resulting solution was dialyzed for two days using DMSO/DDW (1:1) and two days using DDW and freeze-dried for three days. The DS as determined by the $^1$H-NMR spectrum is 11.27%.

Example 6

Synthesis of other HA-Linker-Drug Conjugates

Various HA-linker-drug conjugates were synthesized using protocols similar to those described above, and the degree of substitution and substitution efficiency are summarized in Table 4 below.

TABLE 4

| Drug | Amount (eq) | Linker | DS (%) | Substitution efficiency (%) |
|---|---|---|---|---|
| Cholesterol | 0.2 | β-Ala | 20.0 | 100.0 |
| Cholesterol | 0.2 | Gly | 20.0 | 100.0 |

TABLE 4-continued

| Drug | Amount (eq) | Linker | DS (%) | Substitution efficiency (%) |
|---|---|---|---|---|
| Testosterone | 0.2 | β-Ala | 16.26 | 81.30 |
| Testosterone | 0.4 | β-Ala | 23.90 | 59.75 |
| Testosterone | 0.6 | β-Ala | 17.94 | 29.90 |
| Budesonide | 0.15 | β-Ala | 14.43 | 96.20 |
| Dexamethasone | 0.4 | β-Ala | 22.61 | 56.52 |
| Triamcinolone acetonide | 0.3 | β-Ala | 30.85 | 102.80 |
| Celecoxib | 0.16 | Urea | 4.45 | 27.81 |

For synthesizing HA-Gly-Cholesterol, 500.0 mg of HA was dissolved in 70 mL DDW; then, 90 mL DMSO was added to the HA solution, and the solution was continuously stirred until it reached room temperature. 247.7 mg of Oxyma and 113.0 mg of NH$_2$-Gly-Cholesterol were dissolved in 10 ml DMSO and added to the HA solution. Then, 405 μl of DIC was slowly added to the HA solution, and the reaction mixture was stirred for 24 hours. The resulting solution was purified using sequential dialysis against the DMSO-water (50%/50% v/v), 0.3 M NaCl aqueous solution, and pure water, followed by freeze-drying. The DS was determined using indirect quantification of the dialysate with HPLC.

For synthesizing HA-β-Ala-Cholesterol, 500.0 mg of HA was dissolved in 70 ml DDW; then, 90 mL DMSO was added to the HA solution, and the solution was continuously stirred until it reached room temperature. 247.7 mg of Oxyma and 116.6 mg of NH$_2$-β-Ala-Cholesterol were dissolved in 10 ml DMSO and added to the HA solution. Then, 405 μL of DIC was slowly added to the HA solution, and the reaction mixture was stirred for 24 hours. The resulting solution was purified using sequential dialysis against the DMSO-water (50%/50% v/v), 0.3 M NaCl aqueous solution, and pure water, followed by freeze-drying. The DS was determined using indirect quantification of the dialysate with HPLC.

For synthesizing HA-β-Ala-Testosterone, 100.0 mg of 360K HA was dissolved in 10 ml of DDW. Next, 15 mL of DMSO was added to the HA solution. Then, 36 mg of Oxyma was dissolved in 1 ml DMSO and added to the HA solution; the reaction mixture was stirred for 6 minutes. Then, 17.8 (0.2 eq), 35.8 (0.4 eq), or 53.7 (0.6 eq) mg of the Testosterone-β-Ala-NH$_2$ was added to the HA solution; then, the reaction mixture was stirred for 1 minute. Next, 81 μL DIC was dissolved in 1 ml DMSO and then added to the HA solution; the reaction mixture was allowed to react for 24 hours at room temperature; the resulting solution was dialyzed for four days and then freeze-dried for three days.

For synthesizing HA-β-Ala-Budesonide, 360K HA (1000.0 mg) was dissolved in 100 ml of DDW. Next, 110 ml DMSO was added to the HA solution, and the solution was continuously stirred until it reached room temperature. 170 mg of Budesonide-β-Ala-Boc was de-protected. Then, 500 mg of Oxyma and the Budesonide-β-Ala-NH$_2$ were added to the HA solution; then, the reaction mixture was stirred until it became uniform. Next, 810 μL DIC was slowly added to the HA solution under the level; the reaction mixture was allowed to react for 24 hours at room temperature; the resulting solution was dialyzed and then freeze-dried.

For synthesizing HA-β-Ala-Dexamethasone, 100.0 mg of HA (0.25 mmol) was dissolved in 8 ml DDW; then, 15 ml DMSO was added to the HA solution (Bottle A). 53 mg of Boc-β-Ala-Dexamethasone (0.1 mmol) was de-protected, neutralized, and then dissolved in 5 mL DMSO, followed by adding 50 mg of Oxyma (Bottle B). Bottle A and Bottle B were mixed, and then, 80 μl of DIC was slowly added to the HA solution, and the reaction mixture was stirred for 24 hours. The resulting solution was dialyzed and freeze-dried. For synthesizing HA-β-Ala-Triamcinolone acetonide, 400.0 mg of HA (1 mmol) was dissolved in 6 ml DDW; then, 18 mL DMSO was added to the HA solution (Bottle A). 180 mg of Boc-β-Ala-Triamcinolone acetonide (0.3 mmol) was deprotected, neutralized, and then dissolved in 5 mL DMSO, followed by adding 200 mg of Oxyma (Bottle B). Bottle A and Bottle B were mixed, and then 320 μL of DIC was slowly added to the HA solution, and the reaction mixture was stirred for 24 hours. The resulting solution was dialyzed and freeze-dried.

For synthesizing HA-Urea-Celecoxib, 100 mg of 360K HA was dissolved in 10 ml of DDW. Next, 15 ml DMSO was added to the HA solution. Then, 36 mg of Oxyma was dissolved in 1 ml DMSO and added to the HA solution; the reaction mixture was stirred for 6 minutes. Then, 20 mg of Celecoxib-linker-$NH_2$ was dissolved in 1 ml DMSO and then added to the HA solution; then, the reaction mixture was stirred for 1 minute. Next, 81 μL DIC was dissolved in 1 ml DMSO and then added to the HA solution; the reaction mixture was allowed to react for 24 hours at room temperature; the resulting solution was dialyzed for four days and then freeze-dried for three days.

It will be understood that the above description of embodiments is given by way of example only and that those with ordinary skill in the art may make various modifications. The above specification, examples, and data provide a complete description of the structure and use of exemplary embodiments of the invention. Although various embodiments of the invention have been described above with a certain degree of particularity or with reference to one or more individual embodiments, those with ordinary skill in the art could make numerous alterations to the disclosed embodiments without departing from the spirit or scope of this invention.

What is claimed is:

1. A method for synthesizing a hyaluronan-drug conjugate, comprising the steps of:
   preparing a drug solution by dissolving a plurality of drug molecules in dimethyl sulfoxide (DMSO);
   preparing an additive solution by dissolving an additive in DMSO, wherein the additive is ethyl cyano(hydroxyimino)acetate;
   preparing a hyaluronan solution by dissolving a plurality of hyaluronan molecules in water and DMSO;
   mixing the drug solution, the additive solution, the hyaluronan solution, and diisopropylcarbodiimide (DIC) to obtain a reaction mixture; and
   allowing components in the reaction mixture to react, thereby forming the hyaluronan-drug conjugate.

2. The method for synthesizing a hyaluronan-drug conjugate of claim 1, wherein at least one the plurality of drug molecules has or is modified to have at least one amino group.

3. The method for synthesizing a hyaluronan-drug conjugate of claim 2, wherein the amino group is a primary amine.

4. The method for synthesizing a hyaluronan-drug conjugate of claim 2, wherein the at least one drug molecule is modified with one or more amino acids or urea.

5. The method for synthesizing a hyaluronan-drug conjugate of claim 4, wherein the amino acid is β-alanine (β-Ala) or glycine.

6. The method for synthesizing a hyaluronan-drug conjugate of claim 4, wherein the step of mixing the drug solution, the additive solution, the hyaluronan solution, and DIC to obtain the reaction mixture comprises the steps of:
   preparing a hyaluronan/additive solution by mixing the additive solution with the hyaluronan solution;
   mixing the drug solution with the hyaluronan/additive solution; and
   adding DIC into the hyaluronan/additive solution.

7. The method for synthesizing a hyaluronan-drug conjugate of claim 1, wherein at least one the plurality of drug molecules has or is modified to have a carboxylate group.

8. The method for synthesizing a hyaluronan-drug conjugate of claim 7, wherein the at least one drug molecule is modified with a $C_2$-$C_{20}$ dicarboxylic acid.

9. The method for synthesizing a hyaluronan-drug conjugate of claim 7, wherein at least one the plurality of hyaluronan molecules is modified with a linker.

10. The method for synthesizing a hyaluronan-drug conjugate of claim 9, wherein the linker is a dihydrazide.

11. The method for synthesizing a hyaluronan-drug conjugate of claim 1, wherein the hyaluronan molecules have a weight-average molecular weight (Mw) of about 5 kilodaltons (kDa) to 500 kilodaltons (kDa).

12. The method for synthesizing a hyaluronan-drug conjugate of claim 1, wherein the hyaluronan molecule is a hyaluronic acid (HA) molecule, or a derivative or salt thereof.

13. The method for synthesizing a hyaluronan-drug conjugate of claim 1, wherein the hyaluronan-drug conjugate has a degree of substitution with the drug molecule of 0.5 to 70%.

14. The method for synthesizing a hyaluronan-drug conjugate of claim 1, wherein the drug molecule is a steroid drug, nucleoside or nucleotide analog, non-steroid anti-inflammatory drug (NSAID), cytotoxic drug, or immunomodulator.

15. The method for synthesizing a hyaluronan-drug conjugate of claim 14, wherein the steroid drug is cholesterol, cortisone, hydrocortisone, prednisolone, methylprednisolone, dehydroepiandrosterone, triamcinolone, dexamethasone, betamethasone, triamcinolone acetonide, budesonide, estrone, estradiol, estriol, testosterone or 11-deoxycorticosterone.

16. The method for synthesizing a hyaluronan-drug conjugate of claim 14, wherein the nucleoside or nucleotide analog is a deoxyadenosine analog, adenosine analog, deoxycytidine analog, guanosine analog, deoxyguanosine analog, thymidine analog, deoxythymidine analog, or deoxyuridine analog.

17. The method for synthesizing a hyaluronan-drug conjugate of claim 14, wherein the NSAID is aspirin, ibuprofen, nimesulide, diclofenac, mefenamic acid, naproxen, sulindac, ketorolac, ketoprofen, tenoxicam, indomethacin, valdecoxib, celecoxib, etoricoxib, or rofecoxib.

18. The method for synthesizing a hyaluronan-drug conjugate of claim 14, wherein the cytotoxic drug is azacytidine, belinostat, bendamustine, brentuximab vedotin, bleomycin, bortezomib, busulfan, carboplatin, carmustine, cyclophosphamide, cytarabine, dacarbazine, dactinomycin, daunorubicin, decitabine, deferoxamine, doxorubicin, epirubicin hydrochloride, fludarabine, fotemustine, fulvestrant, gemcitabine, idarubicin, ifosfamide, irinotecan hydrochloride, ixabepilone, melphalan, methotrexate, oxaliplatin, paclitaxel, pemetrexed, pentostatin, raltitrexed, romidepsin, temozolomide, thiotepa, topotecan, trabectedin, trastuzumab or vinblastine.

19. The method for synthesizing a hyaluronan-drug conjugate of claim 14, wherein the immunomodulator is lenalidomide, pomalidomide, or thalidomide.

* * * * *